United States Patent [19]

Peters

[11] Patent Number: 5,139,479
[45] Date of Patent: Aug. 18, 1992

[54] ANKLE SLEEVE

[75] Inventor: Helena Peters, Bromma, Sweden

[73] Assignee: Camp International, Inc., Jackson, Mich.

[21] Appl. No.: 692,198

[22] Filed: Apr. 26, 1991

[51] Int. Cl.$^5$ ............................................. A61F 5/00
[52] U.S. Cl. ........................................ 602/27; 602/65
[58] Field of Search ............... 128/80 H, 80 C, 80 R, 128/DIG. 15, 165, 166; 2/162, 170, 167, 59, DIG. 7; 602/27, 62, 63, 65

[56] References Cited

U.S. PATENT DOCUMENTS

| | | |
|---|---|---|
| 3,050,053 | 8/1962 | Peckham . |
| 3,312,219 | 4/1967 | Peckham . |
| 3,506,000 | 4/1970 | Baker . |
| 3,926,186 | 12/1975 | Nirschl . |
| 4,013,070 | 3/1977 | Harroff . |
| 4,084,586 | 4/1978 | Hettick . |
| 4,367,733 | 1/1983 | Stromgren . |
| 4,495,942 | 1/1985 | Palumbo . |
| 4,832,010 | 5/1989 | Lerman . |
| 4,878,504 | 11/1989 | Nelson . |
| 4,961,418 | 10/1990 | McLaurin-Smith . |

Primary Examiner—Richard J. Apley
Assistant Examiner—Linda C. M. Dvorak
Attorney, Agent, or Firm—Price, Heneveld, Cooper, DeWitt & Litton

[57] ABSTRACT

There is disclosed a ready-to-wear ankle support adapted to be pulled over the foot and positioned about the ankle area. The ankle support is prepared from a resilient flexible material which is preferably elasticized fabric laminate having a low moisture-absorbent elasticized fabric inner (next to the skin) liner and a moisture-absorbant outer layer comprising an elasticized fabric having a brushed looped texture. The support includes an infinitely adjustable tibia closure and an integral wrap strap which is provided with hook fastening means for releasable attachment to the loop fastening means of the outer surface. The wrap strap is drawn about the support in a figure 8 wrap to provide a desired level of compression to the affected area.

10 Claims, 2 Drawing Sheets

ANKLE SLEEVE

BACKGROUND OF THE INVENTION

This invention relates generally to orthotic supports for use on parts of the body that have been injured and also in preventing injuries before they occur. More particularly, the orthotic supports of this invention are adapted for preventing and relieving injuries to the muscles and tendons of the foot.

Persons engaged in physical activities, particularly athletic activities such as tennis, squash, racketball and the like, often incur muscular injuries to the foot and, in particular, the ankle region. Ankle injuries can occur also from such mundane activities as walking, riding bicycles, exiting from motor vehicles and the like. The primary symptom of these injuries is a chronic inflammation of the attachment of muscle-tendon groups to the associated bones. It is considered that injuries to the foot occur because the normal arrangement of the muscles and their attachments to the associated bone structure predisposes individuals to injury during the movements associated with strenuous physical exercise, such as engaging in tennis, baseball, football, basketball and the like. These exertions create great pressure against the attachment of the muscles mass, subjecting it to repetitive and chronic strain with a subsequent formation of non-elastic scar tissue. The scar tissue often tears again, and tends to become reinflamed The situation is compounded by the lack of appropriate muscle-tendon strength and endurance to withstand the forces which are placed against it. For the most part, the problem occurs because of an inherent weakness in the structure, design or mechanical relationship of the muscles, tendons or ligaments in the foot which subject the ankle area, in particular, to increased forces in a specific area, thus, placing an inordinate strain on the tissues.

A number of bandage-like devices, generally elastic in nature, have been developed which can be placed about the foot. Such devices have suffered from several disadvantages. For example, some elastic devices have tended to restrict circulation in limbs, and elastic characteristics of such bandages have failed to provide sufficient counter-force pressure to effectively disseminate the concentration of forces. Other devices designed to exert pressure about the ankle area have a disadvantage of limiting mobility of the bodily member and the joints associated therewith. Still, other devices do not stay in place on an extremity and are too narrow to properly disseminate forces placed on the muscles. Some, as the ankle support described in Peckham U.S. Pat. No. 3,312,219, comprise an elaborate plurality of flexible straps or tapes which are secured in a precise predetermined angular pattern which is intended to ensure that each strap is automatically directed into proper position for supporting the limb in the best possible way. Others, such as using adhesive tape and elastic band members such as the well-known "Ace" bandage, require considerable expertise to ensure that the ankle is properly wrapped for correct support while, at the same time, not limiting circulation flow to and from the member.

SUMMARY OF THE INVENTION

The orthotic device of the present invention comprises a ready-to-wear one-piece pull-on ankle support adapted to anatomically conform to the shape of an ankle. The sleeve is constructed of a resilient flexible material, includes a top opening, a bottom opening and an integral elongated wrap strip attached to one edge of one of said openings.

DESCRIPTION OF THE PREFERRED EMBODIMENTS

Figure 1:
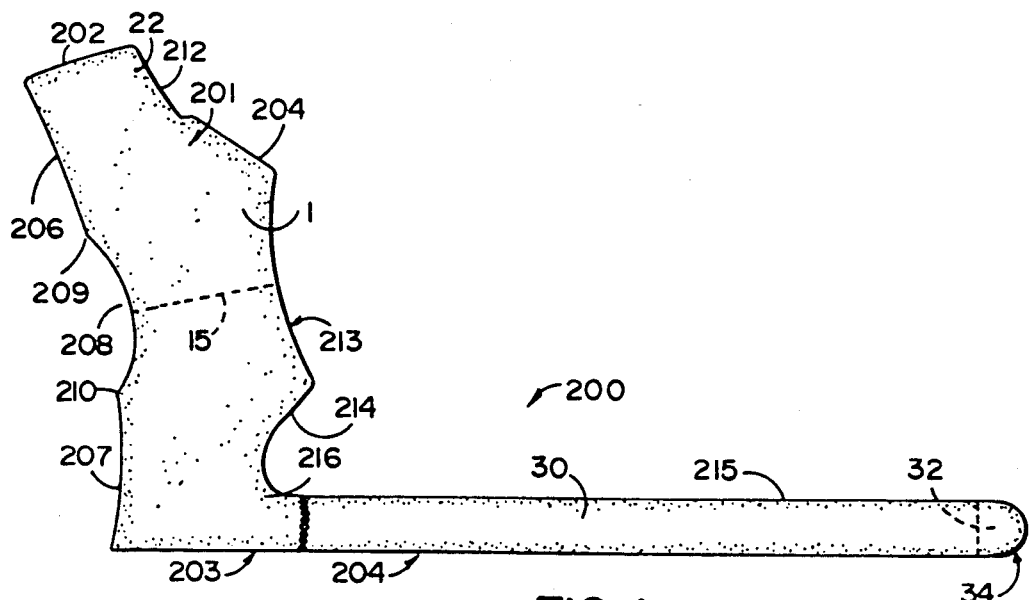
FIG. 1 is a planar view of the cutout material which is utilized in forming the integral one-piece ankle wrap of this invention.
Figure 2:
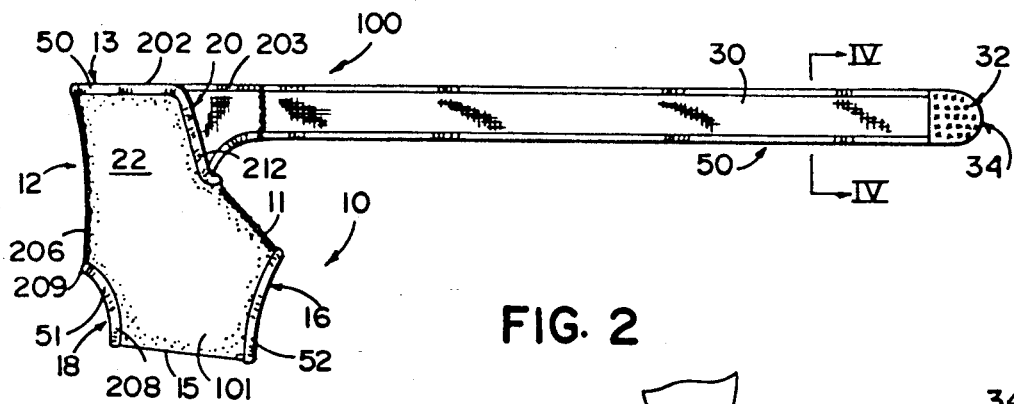
FIG. 2 is a side elevation of the integral one-piece ankle wrap which has been manufactured from a pattern such as shown in FIG. 1.
Figure 4:
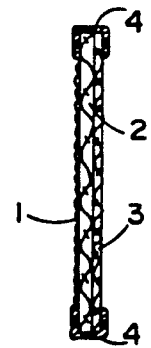
FIG. 4 is a cross-sectional view of the elasticized fabric composite taken along the plane IV—IV of FIG. 2.

In the preferred embodiments, the support comprises an ankle-shaped sleeve 10 having a heel opening 18, a toe opening 16 and an enlarged U-shaped tibia opening 20. One side of the tibia opening 20 provides a tab 22 having a free end which permits for substantially infinite adjustment of closure to accommodate for variations in the girth of the leg at the tibia. The other side of the tibia opening 20 merges into an integral elongated proximal wrap strip 30 adapted to be wrapped about the ankle area in a FIG. 8 configuration.

At least a portion of the exposed outer surface 1 comprises a brushed texture having looped fastening means. The elongated strap 30 is provided at its free end 34 on its inner surface 3 with a pad 32 comprising hooked fastening means for cooperative releasable engagement with the looped fastening means of the outer surface 1.

In operation, the sleeve 10 is pulled on over the foot and, when properly positioned in the ankle area, the strap 30 is then wrapped around the ankle and foot in a FIG. 8 wrap and the end is secured.

The combined sleeve and wrap 10 of the present invention is of simple construction. It can be cut from a single piece of material, but for cost considerations is cut into two pieces which are joined to form a unitary support member. The sleeve 10 is formed from flexible resilient material which itself provides a degree of support and the subsequent wrapping of the strap 30 about the foot in a FIG. 8 fashion allows even one with no expertise to apply a comfortable amount of compression to the ankle area. Ankle wraps of this invention are generally intended to be wrapped towards the outside of the ankle, thus, making it particularly suitable for inversion strains. However, by using the ankle wrap 10 intended for the opposite foot, one can reverse the direction in which the member is wrapped, thereby accommodating to eversion sprains as well.

The ankle support of the invention is formed from a resilient flexible material comprising an exposed outer surface or layer and an inner layer or surface adapted to be worn next to the body area. More particularly, the supports of this invention can be formed from substantially any natural or synthetic material, including both inelastic and elastic materials, having sufficient flexibility and resiliency to enable the support to anatomically conform to the body member to which it is applied In addition, the supports include mutually intercooperating connector means comprising loop keeper means on at least a portion of the outer surface of the support and a companionate array of hook keeper means on at least a portion of the inner surface of the support which confront the loop keeper means when both keeper means are in an overlying relationship on the supports; the hook means being adapted in response to pressure against the loop means to intermesh with the loop means and releasably cling to the loop means, to be separated therefrom in response to a peeling quick yanking force.

The resilient flexible natural or synthetic materials suitable for use in the practice of the invention include fabrics made from inelastic fibers such as nylon fibers, polyester fibers, cotton fibers and the like; elastomers such as natural rubber, neoprene rubber and the like; and elasticized fibers comprising a blend of at least one inelastic fiber, such as nylon, polyester, cotton and the like and at least one elastomeric fiber, such as those sold under the trademark Lycra, and including combinations of two or more natural and/or synthetic materials, generally in the form of a laminated structure.

The preferred material comprises a flexible resilient elasticized fabric laminate comprising an outer elasticized fabric layer, an open-cell polymeric foam core and an inner or proximal elasticized fabric layer. The foam core is coextensive with and adhered to both inner and outer layers. The laminate is stretchable in all directions. The inner and outer layers comprise elasticized fabrics having substantially the same degree of stretch in all directions. The outer elasticized fabric layer is preferably a high moisture absorbent fabric comprising a blend of at least one inelastic fiber and at least one elastic fiber, with a blend of inelastic polyamide and elastic polyurethane being currently preferred The outer surface has a brushed felt-like texture comprising myriad upstanding and relatively free fiber loop fastening means. The inner layer is preferably a lower moisture absorbent but good wicking fabric comprising an elasticized cotton fabric comprising a blend of cotton and at least one elastic fiber, preferably an elastic polyurethane fiber The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastic fiber and 5 weight percent open-cell polyethylene foam, based on total weight of the composite. The provision of elasticized fibers and fabrics from different natural and synthetic fibers is well-known in the art, and there is no need for elaboration The composite is lightweight, stretchable to anatomically conform to the body member, durable and easily laundered in home washing machines Drip-drying is the preferred method of drying laundered supports. The high-absorbent elasticized outer layer, the open-cell polymeric foam core and the low-absorbent elasticized inner layer cooperatively provide a breathable composite which aids in the transfer of moisture, such as perspiration from the wearer's body to the outer surface of the outer or exposed layer, which has sufficient porosity to enable moisture to be wicked from the body to the outer surface of the support The elasticized cotton inner layer ensures dryness, provides a comfortable feel against the body and a feeling of soothing warmth for injured and arthritic joints when engaging in strenuous activities while minimizing heat buildup during such activities.

Referring now to the drawings, wherein like reference numbers designate the same part in each of the views, the preferred embodiment of the invention is a flexible elasticized fabric sleeve having an enlarged tibial opening at the top front which facilitates slipping over the foot and an integral elongated wrapping strap. Support 100 is comprised of an open-toed sleeve 10 having a front seam 11, a back seam 12, a top edge 13, a bottom edge 15, a toe opening 16, a heel opening 18, an enlarged tibial opening 20, and a tibial closure tab 22, together with an elongated principal strap member 30 having a fastening member 32 at its free end 34. Also, included is binding 50 around the enlarged tibial entry opening, the top of sleeve 10 and around the entire periphery of ankle strap 30 and bindings 51 and 52 for heel openings and toe openings, respectively The elasticized fabric composite comprises an outer elasticized fiber layer 1, a polymeric open-celled foam center 2 and an elasticized inner layer or liner 3, with the foam center 2 being adhered to both inner and outer layers and having peripheral edges covered by a stitched elasticized binding 4. The laminate is stretchable in all directions. The inner and outer layers comprise elasticized fabrics having substantially the same degree of stretch in all directions. The outer elasticized fabric layer 1 comprises a blend of at least one inelastic fiber and at least one elastic fiber, with a blend of polyamide and elastic polyurethane being currently preferred. The outer surface has a brushed felt-like surface having looped fastening means. The inner layer 3 comprises an elasticized cotton fabric comprising a blend of cotton and at least one elastic fiber, preferably an elastic polyurethane fiber. The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastomeric fiber, and 5 weight percent polyethylene open-celled foam, based on total weight of the composite.

Referring specifically to the various figures, FIG. 1 shows a die-cut pattern from which the ankle support is sewn together. As shown in FIG. 1, pattern 200 comprises an irregularly-shaped main body generally indicated by numeral 201 having outer side 1 appearing to the viewer. Body 201 includes a substantially straight first top edge 202, and a substantially straight second top edge 203 which merges into substantially straight top edge 204 of elongated proximal wrap strap 30 extending away from the main body 201 along the lateral extension of edge 203. Main body 201 also includes rear edges 206 and 207 which are mirror images of each other. Edges 206 and 207 are contoured to conform substantially to the shape of the tendon at the back of the foot. In the pattern of FIG. 1 located between edges 206 and 207 is a substantially semicircular convex recess 208 extending between the points 209 and 210. At its other end at edge 202 arcuate edge 212 tangentially merges with edge 202 to form the tongue or tibia closure tab 22. Edge 212 merges with edge 204a which joins with a shallow concave edge 213 which in turn merges with the generally concave arcuate edge 214. Edge 214 is tangentially radially merged into lower edge 215 of strap 30. Thus, extension 216 of main body 201 merges into strap 30 which is attached to extension 216.

To form ankle support 100 from pattern 200, edges 206 and 207 are placed in abutting relationship to form a line joint, which is stitched to form back seam 12 and heel opening 18 in the sleeve 10 of support 100. The edge 204a is brought into abutting relationship with edge 214 and the resulting line joint is stitched to form arch seam 11, at the same time forming tibia opening 20. Seam 11 generally extends from the base of the ankle area along the top of the foot's arch along the center line of the foot. Seam 11 also results in joining the opposite ends of edge 213 to form open toe opening 16. Seam 11 further merges the arcuate edge 214 into lower edge 215 of leg 30 to form tibial adjustment opening 20 of support 100. Elastic bindings 50, 51 and 52 are stitched to all exposed edges preferably before forming the sleeve.

Figure 3:
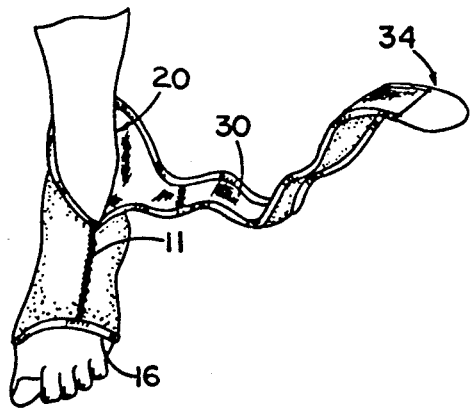
FIG. 3 is a front elevation of the integral one-piece ankle wrap being applied to an ankle.
Figure 5:
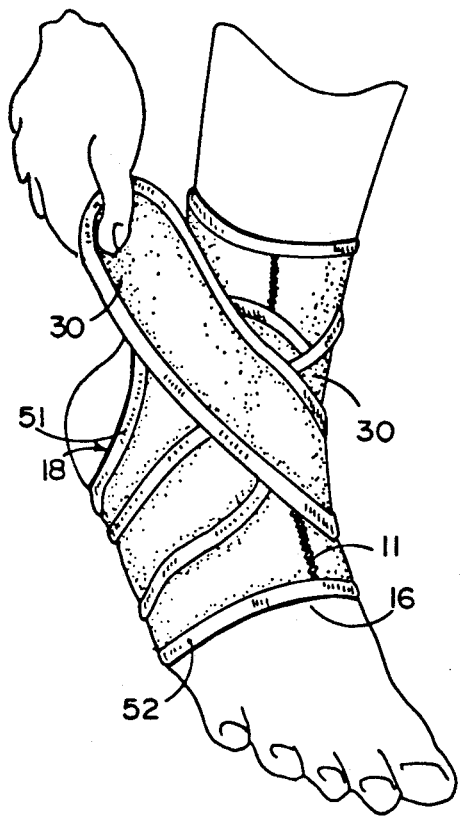
FIG. 5 is a perspective illustrating the applying of the wrap about the ankle.
Figure 6:
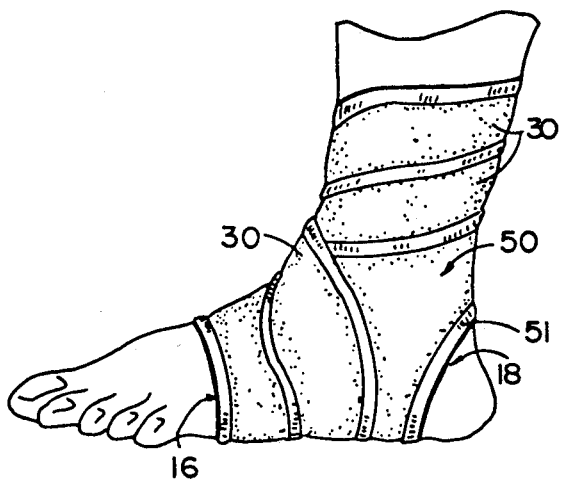
FIG. 6 is a side elevation with the wrap on an ankle.
Figure 7:
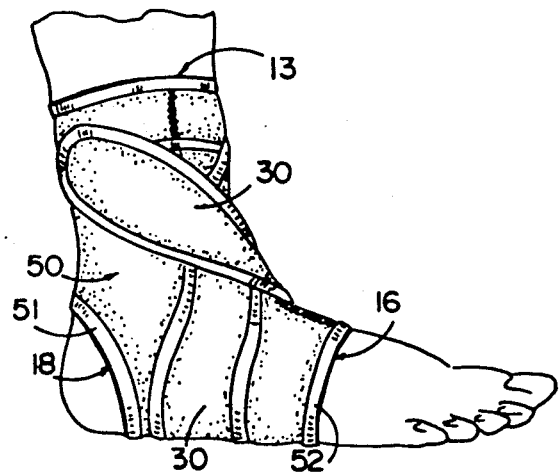
FIG. 7 is the opposite side view of the ankle-wrap on an ankle.

As can be seen by FIG. 3, the sleeve body can be readily applied to the foot with substantially no discomfort because of the elasticized nature of the fabric. The enlarged tibial opening enhances the ease with which one may put on the sleeve and allows for adjustment resulting from differences in circumference of the tibial area, depending upon the size and bone structure of the user. As illustrated in FIGS. 5, 6 and 7, the elongated wrap provides for convenient FIG. 8 wraparound about the foot to apply the proper degree of compression prior to engaging the hook keeper means 32 to the loop keeper means of outer fabric 1. Combining the ankle support with the integral FIG. 8 wraparound strap simplifies application of the FIG. 8 strap while improving the amount of medial and lateral control one is able to obtain because the FIG. 8 support is actually a component of the primary sleeve.

While a single embodiment of this invention has been disclosed with particularity above, numerous modifications of the same within the scope of the invention will be readily apparent to those skilled in the art. Thus, it is considered that various configurational modification of the ankle wrap of this invention will occur to those skilled in the art and are considered also to be encompassed by this invention. Further, the scope of the invention of this muscular support, which is suitable for the treatment and prevention of injuries to muscles in the foot area, is to be limited solely by the claims appended hereto.

The embodiments of the invention in which an exclusive property or privilege is claimed are defined as follows:

1. An ankle support comprising:
   a sheet of elasticized resilient fabric shaped to define a main body with opposite seam edges which are seamed together to define a sleeve, and an elongated ankle wrap strap integral with and extending from said main body adjacent and above one of said seam edges;
   said main body including a tibia closure portion defined by a tibia closure edge extending above the other of said seam edges;
   said sleeve including a top opening above said seamed together edges and a bottom opening below said seamed together edges,
   said top opening being defined in part by said tibia closure portion and said elongated ankle wrap strap whereby said top opening can be partially closed and made more snug after said sleeve has been applied over a user's ankle, by wrapping said elongated ankle wrap strap over said tibia closure portion of said main body.

2. The support of claim 1 in which a heel opening is provided between said top opening and bottom opening.

3. The support of claim 1 in which the sleeve has an inner surface which contacts the body member and an outer exposed surface, said outer exposed surface having a fastening means comprising loops, said wrap strap having end portions with fastening means comprising hooks whereby when wrapped around said body member said end portions can be fastened to said outer exposed surface of said sleeve.

4. The support of claim 1 wherein said sheet of elasticized resilient fabric is constructed of a resilient, flexible, elasticized laminated material, said laminate comprising an elasticized outer layer, the entire outer exposed surface of said outer layer being provided with fastening means comprising loops, and an inner layer comprising an elasticized cotton material and a polymeric cellular open-celled foam body interspersed between and adhered to each of said inner and outer elasticized fabrics, and wherein the end portion of said elongated ankle wrap strap is provided with fasteners of the hook type.

5. The ankle support of claim 1 in which said main body of said sheet of fabric and said elongated ankle wrap strap of said sheet of fabric are integrated by a seam therebetween.

6. The ankle support of claim 1 in which the said top opening has in part an upper edge portion extending along the major portion of said top opening, and said tibia closure edge extends downwardly from said upper edge portion opposite the juncture of said ankle wrap strap and said main body to define with said juncture area a "V" shaped opening portion of said top opening extending downwardly from said upper edge.

7. An ankle support as in claim 1 comprising said elongated ankle wrap strap being of sufficient length and located at a position on said sleeve whereby the wrapping of said elongated ankle wrap strap about said ankle in a FIG. 8 configuration is facilitated, thereby reinforcing the support provided by said sleeve.

8. The ankle support of claim 7 in which said sleeve has an inner surface which contacts the ankle and an outer exposed surface, said outer exposed surface having a fastening means comprising loops, said wrap strap having end portions with fastening means comprising hooks whereby when wrapped around said ankle said end portions can be fastened to said outer surface of said sleeve.

9. The ankle support of claim 7 in which the said top opening has in part an upper edge portion extending along the major portion of said top opening, and said tibia closure edge extends downwardly from said upper edge portion opposite the juncture of said ankle wrap strap and said main body to define with said juncture area a "V" shaped opening portion of said top opening extending downwardly from said upper edge; and said wrap strap is attached to one side of said "V" shaped edge portion.

10. The ankle support of claim 7 wherein said sheet of elasticized resilient fabric is constructed of a resilient, flexible, elasticized material, said laminate comprising an elasticized outer exposed layer, the entire outer surface of said outer layer being provided with fastening means comprising loops; an inner layer comprising an elasticized cotton material; and a polymeric cellular open-celled foam body interspersed between and adhered to each of said inner and outer layers, and wherein the end portion of said elongated ankle wrap strap is provided with fasteners of the hook type.

* * * * *

UNITED STATES PATENT AND TRADEMARK OFFICE
CERTIFICATE OF CORRECTION

PATENT NO. : 5,139,479  
DATED     : August 18, 1992  
INVENTOR(S) : Helena Peters Page 1 of 2

It is certified that error appears in the above-identified patent and that said Letters Patent is hereby corrected as shown below:

Column 1, line 29:
    After "reinflamed" insert --,--.

Column 3, line 2:
   After "applied" insert --,--.

Column 3, line 38:
   After "preferred" insert --,--.

Column 3, line 45:
   After "fiber" insert --,--.

Column 3, line 55:
   After "elaboration" insert --,--.

Column 3, line 58:
   After "machines" insert --,--.

Column 3, lines 66 and 67:
   After "support" insert --,--.

UNITED STATES PATENT AND TRADEMARK OFFICE
CERTIFICATE OF CORRECTION

PATENT NO. : 5,139,479

DATED : August 18, 1992

INVENTOR(S) : Helena Peters

It is certified that error appears in the above-indentified patent and that said Letters Patent is hereby corrected as shown below:

Column 4, line 19:
After "respectively" insert --.--.

Signed and Sealed this

Twenty-sixth Day of October, 1993

Attest:

BRUCE LEHMAN

Attesting Officer

Commissioner of Patents and Trademarks